US008431400B2

(12) United States Patent  (10) Patent No.: US 8,431,400 B2
Hoffmann et al. (45) Date of Patent: Apr. 30, 2013

(54) DERMAL SHEATH CUP CELL POPULATION

(75) Inventors: Rolf Hoffmann, Freiburg (DE); Kevin J. McElwee, West Yorkshire (GB)

(73) Assignee: TrichoScience Innovations Inc., Vancouver (CA)

( * ) Notice: Subject to any disclaimer, the term of this patent is extended or adjusted under 35 U.S.C. 154(b) by 495 days.

(21) Appl. No.: 10/516,031

(22) PCT Filed: Jun. 5, 2003

(86) PCT No.: PCT/DE03/01863
§ 371 (c)(1),
(2), (4) Date: Oct. 18, 2005

(87) PCT Pub. No.: WO03/104443
PCT Pub. Date: Dec. 18, 2003

(65) Prior Publication Data
US 2006/0088505 A1    Apr. 27, 2006

(30) Foreign Application Priority Data
Jun. 5, 2002 (DE) .................................. 102 24 982

(51) Int. Cl.
*C12N 15/02* (2006.01)
*C12N 5/00* (2006.01)

(52) U.S. Cl.
USPC ........... 435/378; 435/383; 435/325; 435/352; 435/353; 435/366

(58) Field of Classification Search ................... None
See application file for complete search history.

(56) References Cited

U.S. PATENT DOCUMENTS

| | | | | |
|---|---|---|---|---|
| 6,497,875 B1 * | 12/2002 | Sorrell et al. | ................ | 424/93.7 |
| 6,887,490 B1 * | 5/2005 | Jahoda et al. | ................ | 424/445 |
| 2003/0077823 A1 * | 4/2003 | Li et al. | ......................... | 435/366 |

FOREIGN PATENT DOCUMENTS

| EP | 1 337 624 | | 9/2006 |
|---|---|---|---|
| JP | 07-274950 | | 10/1995 |
| WO | WO 95/01423 | | 1/1995 |
| WO | WO 99/03505 | * | 1/1999 |
| WO | WO 01/32840 | | 5/2001 |
| WO | WO 02/40645 | | 5/2002 |

OTHER PUBLICATIONS

Lyle et al., Journal of Investigative Dermatology, Symposium Proceedings/the Society for Investigative Dermatology, vol. 4, No. 3, p. 296-301, 1999.*
Akiyama et al., Journal of Investigative Dermatology, vol. 114, No. 2, p. 321-327, 2000.*
Turksen, K., Developmental Cell, vol. 6, No. 4, p. 454-456, 2004.*
Reynolds et al. Trans-gender induction of hair follicles. Reynolds et al., Nature, 402(6757):33-4, 1999.*
Gharzi et al. Plasticity of hair follicle dermal cells in wound healing and induction, Experimental Dermatology 12: 126-136, 2003.*
Jahoda et al., Induction of hair growth in ear wounds by cultured dermal papilla cells, J Invest Dermatol. 101(4):584-90, 1993.*
Chuong, et al., "Dinosaur's feather and chicken tooth? Tissue engineering of the integument," *Eur J Dermatol*, 11:286-292, 2001.
Hutchinson and Thompson, "The cross sectional size and shape of human terminal scalp hair," *Br J Dermatol*, 136:159-165, 1997.
Hutchinson and Thompson, "The size and form of the medulla of human scalp hair is regulated by the hair cycle and cross sectional size of the hair shaft," *Br J Dermatol*, 140:438-445, 1999.
Jahoda, et al., "Induction of hair growth by implantation of cultured dermal papilla cells," *Nature*, 311(5986):560-562, 1984.
Kligman, "The human hair cycle," *J Invest Dermatol*, 31:304-316, 1959.
Messenger, "The culture of dermal papilla cells from human hair follicles," *Br J Dermatol*, 110(6):685-689, 1984.
Oliver, "The induction of hair follicle formation in the adult hooded rat by vibrissa dermal papillae," *J Embryol Exp Morphol*, 23(1):219-236, 1970.
Paus and Cotsarelis, "The biology of Hair follicles," *N Engl J Med*, 341:491-497, 1999.
Reynolds, et al., "Transgender induction of hair follicles," *Nature*, 402(6757):33-34, 1999.
Sperling, "Hair anatomy for the clinician," *J Am Acad Dermatol*, 25:1-17, 1991.
Thesleff, "Genetic basis of tooth development and dental defects," *Acta Odontol Scand*, 58:191-194, 2000.
Bassukas and Hornstein, "Effects of plucking on the anatomy of the anagen hair bulb. A light microscopic study," *Arch. Dermatol. Res.*, 281:188-192, 1989.
Jahoda, "Cell movement in the hair follicle dermis—More than a two-way street?" *The Journal of Investigative Dermatology*, 121(6):9-11, 2003.
Matsuzaki and Yoshizato, "Role of hair papilla cells on induction and regeneration processes of hair follicles," *Wound Rep. Reg.*, 6:524-530, 1998.
Matsuzuki and Yoshizato, "The upper dermal sheath has a potential to regenerate the hair in the rat follicular epidermis," *Differentiation*, 60:287-297, 1996.
Pisansarakit et al., "Cultivation of mesenchymal cells derived from the skin and hair follicles of the sheep: The involvement of peptide factor in growth regulation," *Arch. Dermatol. Res.*, 283:321-327, 1991.
Reynolds and Jahoda, "Hair follicle stem cells? A distinct germinative epidermal cell population is activated in vitro by the presence of hair dermal papilla cells," *Journal of Science*, 99:373-385, 1991.
Reynolds and Jahoda, "Hair matrix germinative epidermal cells confer follicle-inducing capabilities on dermal sheath and high passage papilla cells," *Development*, 122:3085-3094, 1996.
Wu et al., "Enzyme digestion to isolate and culture human scalp dermal papilla cells: a more efficient method," *Arch. Dermatol. Res.*, 297:60-67, 2005.

* cited by examiner

*Primary Examiner* — Deborah Crouch
(74) *Attorney, Agent, or Firm* — Parker Highlander PLLC

(57) ABSTRACT

The present invention relates to a method for isolating hair follicle mesenchymal stem cells and to the use thereof for therapy and prophylaxis as well as for cosmetic treatments.

6 Claims, 5 Drawing Sheets

DERMAL SHEATH CUP CELL POPULATION

Figure 1:
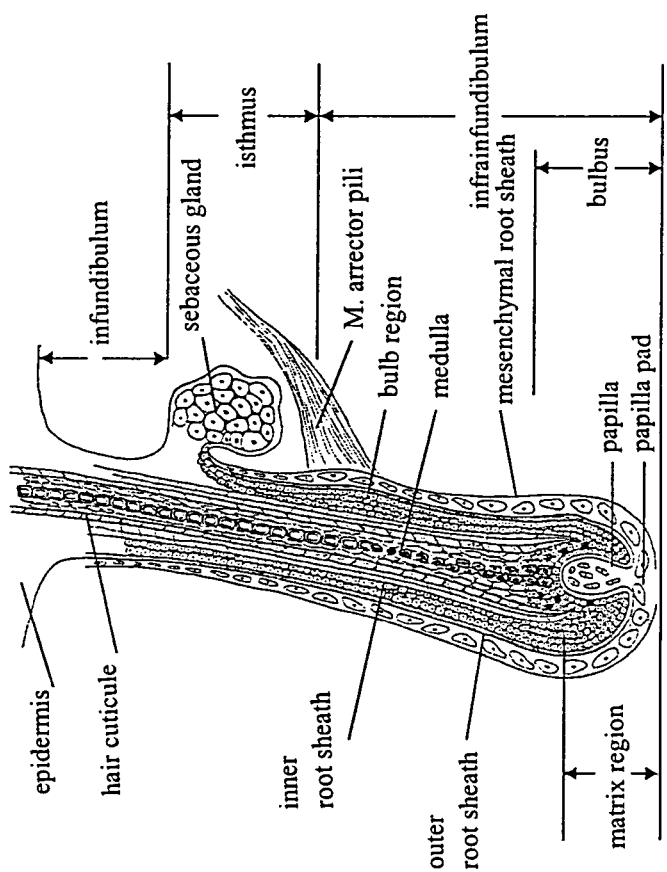

This application claims priority to PCT/DE 2003/001863, filed on Jun. 5, 2003, the entire contents of which are hereby incorporated by reference.

The present invention relates to a method for isolating hair follicle mesenchymal stem cells and to the use thereof for therapy and prophylaxis as well as for cosmetic treatments.

Except for the mucosa, the palms of the hands and the soles of the feet, hair follicles are found on the entire human integument, the hair follicles representing a self-contained, complex functional entity, a miniature-organ. Topographically-anatomically, four portions are distinguished a) infundibulum: section between hair follicle ostium and the intersection of the sebaceous gland into the hair canal; b) isthmus: section between the intersection of the sebaceous gland and the insertion of the M. arrector pili; c) infrainfundibulum (suprabulbar portion): section between the insertion of the M. arrector pili until the bulbus; and d) hair bulbus (hair bulb) including the follicular dermal papilla. One estimates that the scalp encompasses about 100,000 terminal hair follicles, which are dispersed in groups of 3-5 hair follicles, the so called follicular units, over the scalp. These follicular units are surrounded by a collagenous meshwork of fibers and are separated from each other by broader collagen fibers.

The onion-shaped hair bulb forms the proximal end of the growing hair follicle and, in the case of terminal hair, extends into the subcutaneous adipose tissue (FIG. 2a, box). Hair matrix cells located in the hair bulb differentiate, thereby forming the shaft. The cells of the matrix are so called "transit amplifying cells", i.e. a population of cells which dies after a phase of highly proliferative growth. The follicular dermal hair papilla (FIGS. 2b and c) which is supplied by a subtle meshwork of nerves and vessels, arches into the proximal hair bulb and typically has an onion shape. The dermal hair papilla is distinct from the dermis in that it is embedded within an extracellular matrix that resembles a basement membrane with respect to its composition. Therefore, during the growth phase of the hair follicle (so called anagen), single fibroblasts of the dermal hair papilla may directly contact the matrix keratinozytes via cellular appendices. Melanocytes located over the apex of the dermal papilla, show melanogenesis activity, dependent on the hair cycle, from anagen stage IV until the start of the catagen (regression phase). The activity of the matrix keratinocytes is regulated by morphogenic and mitogenic signals with the specialised hair papilla cells. In the case of dysfunctions in this segment of the hair follicle, the growth phase (anagen) is aborted and the follicle enters the regression phase (catagen). This illustrates that processes which destroy the matrix keratinocytes and the overlying bulge area can lead to irreversible loss of hair, whereas noxa that merely affect the function of the papilla cells may determine the size of the papilla and the thickness of the hair shafts to be formed. Therefore, the biggest dermal hair papillae are found in the terminal hair follicles of the beard and increasingly smaller dermal hair papillae are found in androgenetic alopecia affected scalp hair follicles.

The dermal sheath (DS) of the hair follicle consists of two layers of fibroblast-like cells and collageneous fibers, wherein the inner layer is oriented circularly around the hair shaft. The thicker outer part of the mesenchymal root sheath contains collageneous and elastic fibers running parallel to the hair shaft. In addition, a circular meshwork of nerve fibers expanding onto the basement (glassy) membrane can be found, indicating the tactile function of the hair. The mesenchmyal DS merges into the follicular dermal hair papilla at the proximal, hair bulb, end.

The hair shaft is jacket-like surrounded by telescoped epithelial root sheaths. In the length of the intrafollicular hair shaft formation and pigmentation, an inner root sheath (IRS) and an outer root sheath (ORS) can be easily defined in cross-section. The IRS is formed by the outer, mostly two-layered Henle-layer, the middle multilayered Huxley-layer as well as the IRS cuticule. All three layers emerge from matrix cells located at the outer edge of the hair bulb. Whereas the ORS continuously passes into the basal cell layer of the epidermis, the IRS terminates at about the level of the infundibulum. Therefore, the distal changeover to the epidermal coating of the hair follicle ostium shows an epidermal homification. Directly below the aperture of the sebaceous gland the ORS borders on the IRS. One important location of the ORS is the insertion point of the M. arrector pili, the so called bulge. In this region, as well as proximally thereof, the epithelial stem cells of the hair follicle are assumed to have their seat. By means of a horizontal section at the level of the isthmus, terminal hair can be recognised by their—in comparison to IRS cross section—thicker hair shaft and vellus hair by their small cross section diameter hair shafts which are thinner than the IRS.

The hair follicle is composed of two primary cell species. The first cell species is recruited from the embryonic ectoderm/the epidermis at the beginning of the hair follicle morphogenesis, and the other is recruited from mesodermal portions. Whereas the epithelial stem cells of the hair follicle are significantly located within or close to the so called bulge region (insertion point of the hair bulge muscle) of the hair follicle, it was the valid doctrine that the mesenchymal stem cells reside in the dermal papilla. In this regard preceding analyses have shown that prepared dermal papillae may be implanted into hairless segments of the skin, and that this induces the formation of hair follicles (Oliver, 1970, Jahoda et al., 1984, Reynolds et al., 1999). Thereby, the location of the removal of the papilla cells determines the type of the hair formed (e.g. whisker/vibrissa papillae induce whiskers/vibrissae again in a mouse ear). Follicular dermal hair papillae (DP) may also be placed in nutrient medium to increase the cell number. These cultivated DP cells may be implanted into hairless areas of the skin (e.g. palms of the hands) and even there they are able to induce the formation of new hair follicles (Messenger, 1984). The DP cells are indeed able to induce hair, but they do not repopulate the DSC or DS region. DSC means "dermal sheath cup" and indicates the location of the cells according to the invention. Furthermore, the hair formed by DP cells have only a short lifespan.

On the one hand hair loss is a part of the ageing process (senile alopecia), a result of active pathological mechanisms as in the case of the androgenetic alopecia, alopecia areata and scarring/traumatic alopecias, or on the other hand in response to injuries such as the after-effect of a chemotherapy. Hair loss is in general regarded in a negative light by the society. The strong demand for therapy to prevent hair loss or to replace hair has brought forth the development of a multiplicity of different medicaments, products and techniques. In the hair biological research, the DP within the hair follicle entity has been identified as a key structure that determines the development and differentiation of the hair follicle during embryogenesis and that controls both the growth of the hair fiber and the hair follicle cycle. In the case of many hair loss diseases including the most common, androgenetic alopecia, the DP is influenced by exogenous factors leading to the fact that the DP is not able to maintain the vitality of the hair follicle. In part, this might be attributed to a reduction of the size and the loss of cells from the DP. The reduced size of the DP is directly related to the reduced size of hair follicles.

In a simplified way, hair diseases can be defined as "too much" hair (hypertrichosis/hirsutism) or as "too little" hair (all forms of the alopecia such as, but not limited to, alopecia areata, androgenetic alopecia, pseudopelade of Brocq, alopecia due to lichen planopilaris, lupus erythematosus, congenital hypotrichosis and atrichias (papular atrichia and others), diffuse hair loss in case of a metabolic disease like for example a dysfunction of the thyroid gland, alopecias after burn injuries or traumas, alopecias in response to a chemotherapy or other noxa). Among these different alopecias, merely for the androgenetic alopecia, only two approved active agents (finasteride, minoxidil) are available. No active agent affects the stem cells and no agent can guarantee cosmetically acceptable hair growth in all cases. The treatment of hypertrichosis is essentially carried out physically, i.e. destruction of the hair follicle by means of laser therapy or electrolysis. In this case, the inhibition of the stem cell function is more effective.

Therefore, there is a justified demand for means to treat too little hair growth.

The problem of the present invention is solved by the subject-matter described in the patent claims.

The following figures illustrate the invention.

FIG. 1 is a schematic depiction of a terminal hair follicle.

Figure 2:
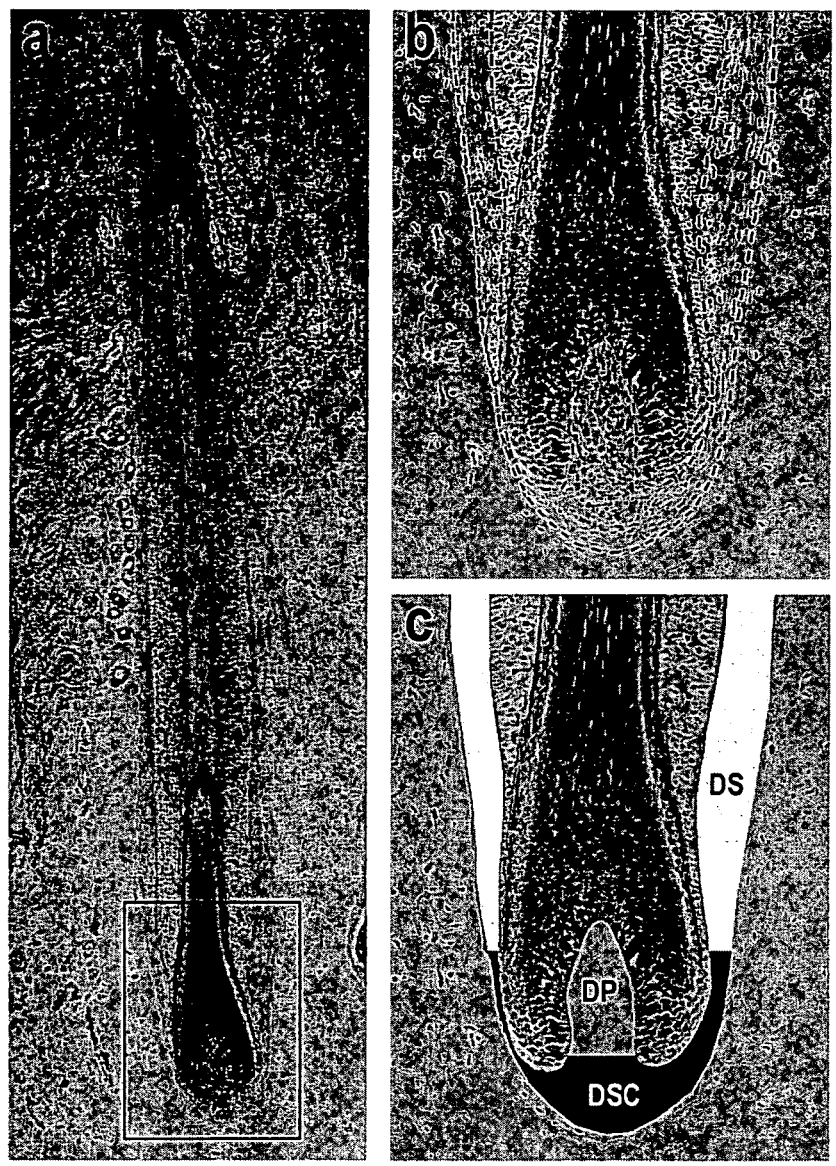

FIG. 2 A shows an anagen hair in a histological section. The frame represents the section which is depicted in FIGS. 2 B and C. DSC means "dermal sheath cup" and indicates the position of the cells according to the invention. The DSC cells are clearly defined in an anatomical-topographical manner by their position within the hair follicle and they are located at the lower pole of the hair bulb in a position which surrounds the hair bulb in a cup-like manner. DP means "dermal papilla". DS means "dermal sheath".

Figure 3:
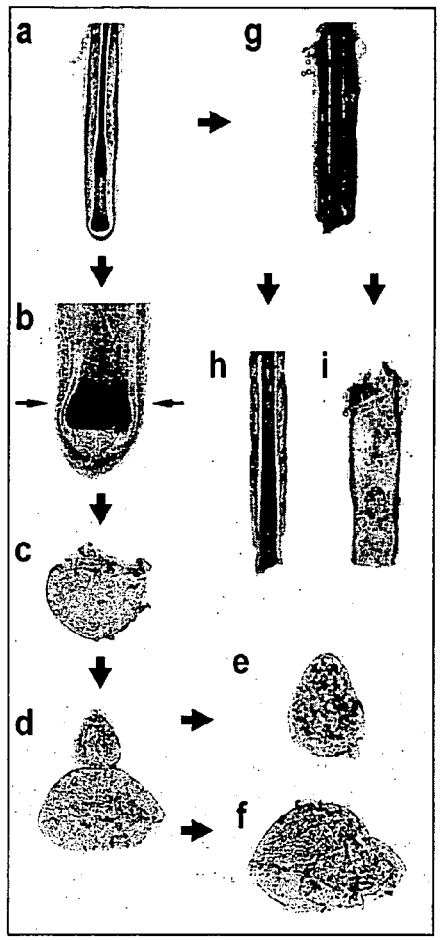

FIG. 3 (*a*) to (*i*) illustrates the single stages of a dissection scheme for obtaining dermal sheath cup cells (DSC). Intact anagen hair (a) are prepared under the stereo microscope. The magnified view in (b) shows the dissection level: a cross-section through the hair is carried out at the upper pole of the pigmented zone; the hair peeling (DSC) which is cup-like attached can be removed along with the DP (c). This tissue part is everted (d) and the DP (e) is separated from the DSC (f). From the remaining non-bulbar parts of the anagen hair follicle (g), the epithelial portions (h) of the hair follicle and the connective tissue coating (i)=dermal sheath=DS remain.

Figure 4:
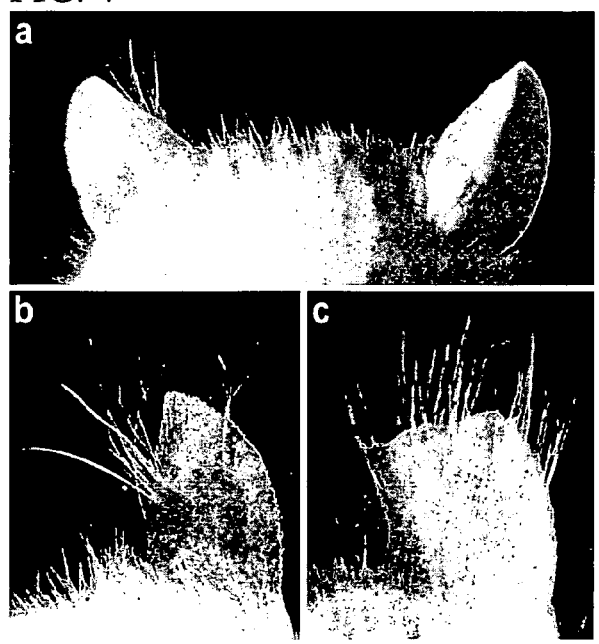

FIG. 4 (*a*) to (*c*) shows in a depiction the result of an implantation of DSC cells in a mouse ear. The isolated DSC tissues were propagated in cell culture and cells were implanted into a mouse ear. After implantation of whisker DSC cells into the right ear, whiskers grew out of this mouse ear. The left untreated ear did not show any hair growth of whiskers. FIGS. 4*b* and 4*c* show the respective magnifications.

Figure 5:
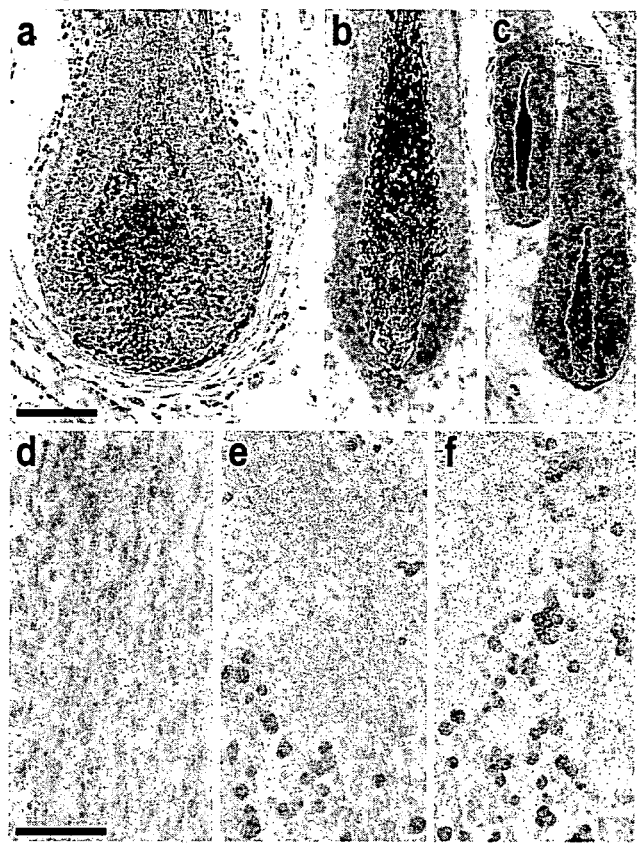

FIG. 5 (*a*) to (*f*) shows the alkaline phosphatase activity. This figure shows the strong expression of the alkaline phosphatase in the dermal hair papilla, whereas the DSC cells exhibit only a weak expression. The expression ends abruptly at the transition from DSC to DS (FIGS. 3 *b* and *c*, FIG. 5 *a-c*). Cultivated cells of the DP (FIG. 5*f*) and DSC (FIG. 5*e*) show an identical growth pattern in vitro which tends to the formation of so called pseudopapillae. The cells of the DS tend to a growth pattern with strongly elongated cells having a fish scale-like arrangement (FIG. 5*d*). The cells of the DP (FIG. 5*f*) show a strong alkaline phosphatase activity, the cells of the DSC (FIG. 5*e*) show a weak alkaline phosphatase activity and the cells of the DS (FIG. 5*d*) show no alkaline phosphatase activity.

Figure 6:
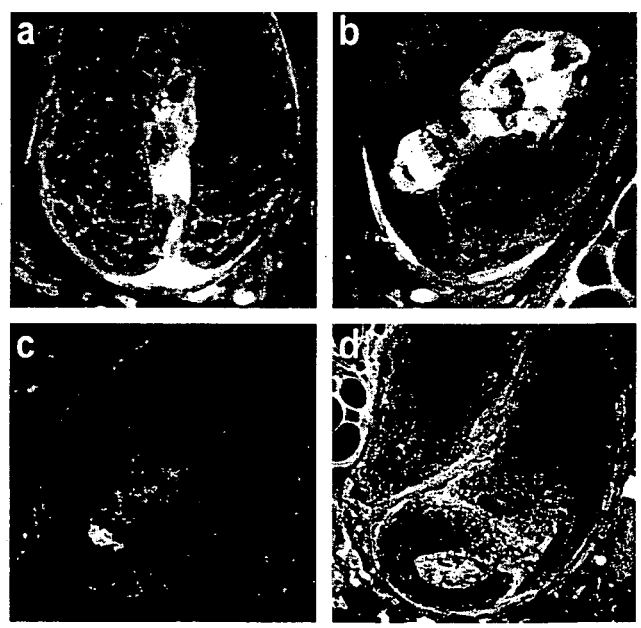

FIG. 6 shows induced and repopulated dermal hair papillae after implantation of DSC cells. Fluorescent DSC cells from TgN-GFPX mice were cultivated as described elsewhere and implanted into SCID mouse ears. After 6 months, new hair growth could be seen (FIG. 4). After implantation, fluorescent cells were found by means of confocal laser microscopy both in the DP and in the DSC region, and in part also within the DS (a, b). Whereas all cells of newly formed papillae showed a fluorescence, others showed a chimeric population of fluorescent and non-fluorescent cells (c, d), indicative of the fact that the DSC cells may populate a pre-existing papilla in order to form a thicker hair therewith.

Figure 7:
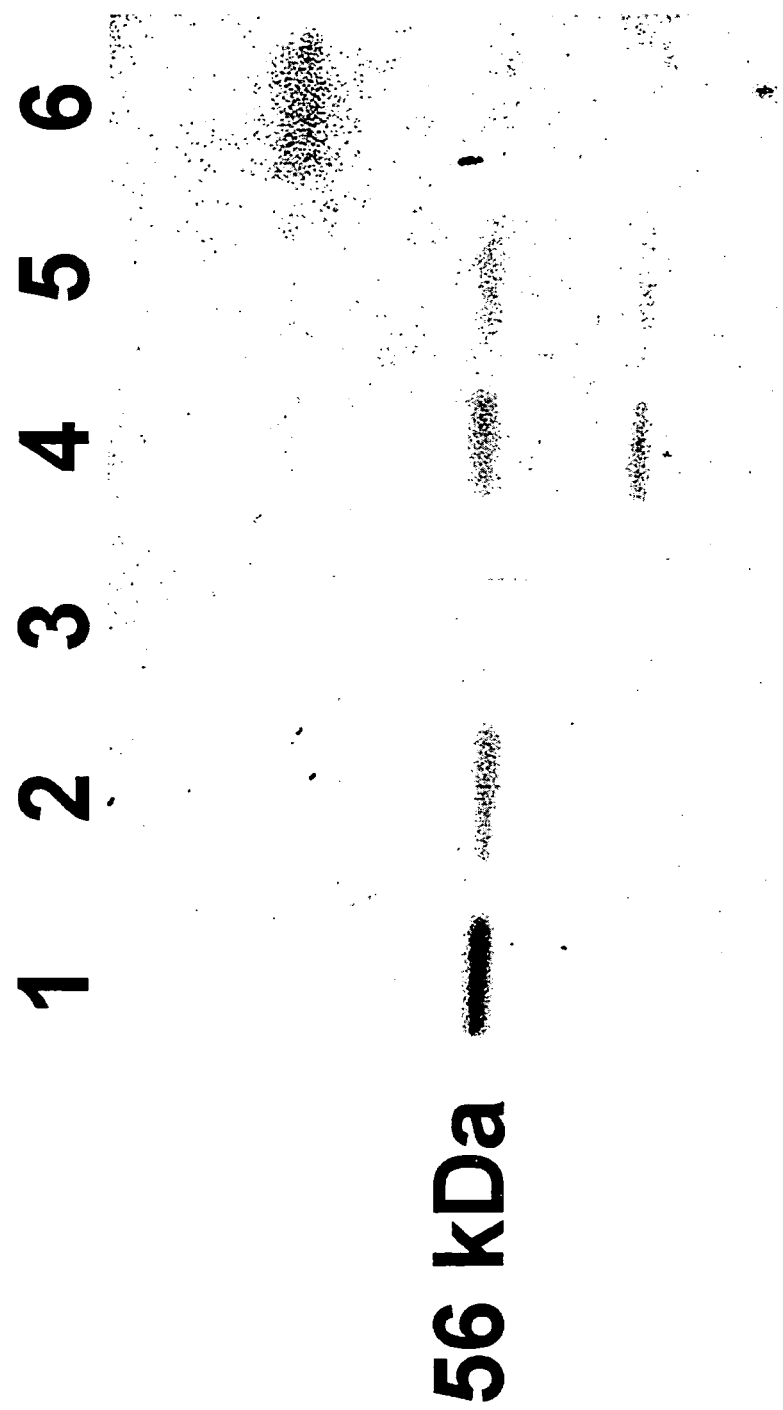

FIG. 7 shows the result of a Western blot for MSP: MSP extracts from cultivated cells of the DP (cytosol=lane 1, membrane bound=lane 4); DSC (cytosol=lane 2, membrane bound=lane 5) and follicular fibroblasts (cytosol=lane 3, membrane bound=lane 6) were chromatographically separated (SDS-PAGE: 12% polyacrylamide) and blotted on a nylon membrane (Hybond ECL, Amersham Biosciences GmbH, Freiburg, Germany). The membranes were blocked with 5% fat-free milk powder and with 0.5% Tween 20 (Sigma-Aldrich, GmbH, Munich, Germany) and washed in PBS. A polyclonal goat anti-human MSP antibody against MSP (HGFL (N-19), sc-6088, Santa Cruz) was used in a ECL detection system (Amersham) according to the manufacturer's instructions. The strong band at 56 kD can be clearly recognised especially in the cells of the DP.

The present invention relates to adult hair follicle mesenchymal stem cells (DSC) having the characteristic of forming a completely new hair follicle DP, of migrating into a pre-existing hair papilla (DP), of forming a part of the dermal connective tissue (DSC and DS) coating and of having less alkaline phosphatase activity than cells of the DP. Preferably, the cells according to the invention originate from a mammal, especially from a mouse, rat, rabbit, guinea pig, goat, pig, bovine or human. The cells according to the invention are able and have the characteristic, respectively, unlike the cells of the follicular connective tissue coating (DS) and the dermal papilla (DP), to form a completely new hair follicle or to migrate into a pre-existing hair papilla in order to produce a bigger and thicker hair therewith. Furthermore, these cells are able and have the characteristic, respectively, to form a part of the dermal connective tissue coating. These two characteristics are neither represented by DS cells nor by DP cells. The adult hair follicle mesenchymal stem cells according to the present invention, in the following also called DSC stem cells or DSC cells, are found around the lower pole of the hair bulb (in the following also called hair bowl or hair cup) in a cup-shaped arrangement, and have therefore been termed dermal sheath cup cells (DSC). The herein used term "adult" in connection with mesenchymal stem cells means that the mesenchymal stem cells are not embryonic stem cells but mesenchymal stem cells isolated from adult organisms.

The cells according to the invention may be characterised biochemically. Therefore, their expression of the alkaline phosphatase was used. Unlike the DP cells, the DSC cells show only limited alkaline phosphatase activity. The DP cells are characterised by the fact that they show a pronounced activity of the alkaline phosphatase during the entire hair cycle. The activity of the alkaline phosphatase is significantly less pronounced in the DSC cells. The DS cells do not show any alkaline phosphatase activity.

In terms of the invention, a low alkaline phosphatase activity means that the activity of DSC cells is lower by about 10%, 15%, 20%, 25%, 30%, 35%, 40%, 45% or 50% in comparison to the DP cells. Furthermore, a lower alkaline phosphatase activity means that the activity of the DSC cells is at least about 10% lower, preferably at least about 15%, 20%, 25%, 30%, 35%, 40%, 45% or 50% lower than the pronounced activity of the alkaline phosphatase in the DP.

The present invention relates to a method for isolating hair follicle mesenchymal stem cells, the method comprising the following steps:
a) preparation of vital hair,
b) cleavage of the hair prepared in step a),
c) isolating the cup shape-like attached hair cup together with the dermal hair papilla,
d) separating the dermal hair papilla from the hair cup,
e) cultivating the hair cup obtained in step d),
f) pooling of the confluent cells.

Preferably, the hair follicles originate from a mammal, especially from a mouse, rat, rabbit, guinea pig, goat, pig, bovine or human. Furthermore, the present invention relates to hair follicle mesenchymal stem cells obtainable by the method according to the invention.

The DSC cells may be isolated by means of the following method. First, a hair follicle is divided to its portions by micro dissection as follows. Thereby, vital hair, e.g. intact anagen hair, are prepared under a dissection microscope. In the case of pigmented hair, a cross-sectional cut is performed through the hair at its upper pole (FIG. 3b, arrows) and the cup shape-like DSC is peeled away together with the dermal hair papilla (DP) (FIG. 3c). This tissue portion is everted (FIG. 3d) and the dermal hair papilla (FIG. 3e) is separated from the hair cup (FIG. 3f). This method may be used not only for the preparation of hair follicle mesenchmyal stem cells but may also be adapted for the preparation of mesenchymal stem cells of the nail and the dental apparatus. The method may be used with all eukaryotic organisms, e.g. with mammals, especially with humans.

The obtained hair cup (DSC) is propagated in cell culture using standard conditions. For example, the cultivation can take place as follows. As medium, AmnioMax C100 basal medium (Gibco) and AmnioMax C100 supplement are used. First, the DSC are cultivated in this medium in 24-well-culture flasks (Falcon, Franklin Lakes, N.J., USA) under sterile and standard conditions (37° C., 5% $CO_2$, 500 µl medium). After a few days, cells grow out spontaneously and are detached with 200 µl/well trypsine-EDTA after reaching a near confluent culture (stopping of the trypsination with 260 µl Amniomax medium/well after detaching all cells) and transferred in 25 ml culture flasks (Greiner, Frickenhausen, Germany). For this, the cells are pooled, centrifuged for 10 minutes at 1000 U/min, the supernatant is discarded and the cells are resuspended in 5 ml Amniomax. The medium is exchanged every 3 days. In order to determine that the obtained cells are the mesenchymal stem cells according to the invention, an alkaline phosphatase detection may be performed. For this, the cells may be cultivated on sterile glass cover slips, fixed in acetone and analysed as described in the examples. The incubation time of the in vitro detection according to the described examples is about 30 minutes to about 1.5 hours, preferably about 1 hour under standard conditions.

With the same method, both the mesenchymal stem cells of the nail and the dental apparatus may be isolated and propagated.

The cells according to the invention may be expanded by means of cell culture, and the cell cultures may be cultivated over several passages. The DSC cells show on the one hand morphological, and on the other hand biochemical, characteristics which can be clearly distinguished from each other. The fibroblasts of the dermal connective tissue coating (DS) show morphologically a typical growth pattern reminiscent of a fish scale-like pattern. The DSC cells grow more compactly, do not form these fish scale-like structures and tend to form so called pseudopapillae, which means, little cell accumulations are built in the cell culture flask that are morphologically reminiscent of a dermal hair papilla (DP). As already mentioned, the fibroblasts of the follicular connective tissue coating (DS) do not express any alkaline phosphatase, the DSC cells express only very little, whereas the DP cells exhibit a strong activity of the alkaline phosphatase in vitro and in vivo.

The connective tissue cells at the lower pole of the connective tissue sheath, the so called hair cup cells (DSC), may regenerate all relevant structures of the hair follicle unit formed by the dermis. Due to this feature, they enable the formation of new hair growth or the formation of a thicker hair by population of a small DP. In this case, the life span of the newly formed hair is not limited in time, but may be a lifelong one in principle. In contrast, such a lifelong regenerative capacity after implantation of DP cells has not been described. All attempts with DP cells are only transient, whereas genuine stem cells having a lifelong possibility to proliferate are introduced into the skin by the implantation of DSC cells.

The present invention relates to hair follicle mesenchymal stem cells according to the invention as a means for the therapy and prophylaxis as well as to cosmetic treatments. Furthermore, the invention relates to the use of the stem cells according to the invention for the preparation of a means for the therapy or prophylaxis of alopecia or for the gene therapy.

The cells obtainable by the method according to the invention may be used for the treatments of an alopecia, in particular, of an Alopecia areata, androgenetic alopecia, pseudopelade of Brocq, alopecia due to lichen planopilaris, lupus erythematosus, a congenital hypotrichosis and atrichia, diffuse hair loss in terms of a metabolic disease, alopecia after burn or trauma or alopecia after a chemotherapy as well as for gene therapy. The application may be performed e.g. by injection of the cells in solution (e.g. physiological saline solution) or by implantation, i.e. embedded in a matrix (e.g. collagen) or packed in liposomes. If a single injection or implantation is not sufficient, after-treatments (repeat treatments) are possible. If certain modes of application are preferred for single skin areas, the cells according to the invention may be administered accordingly.

The respective mesenchymal stem cells of the nail and dental apparatus have the respective features (Chuong et al., 2001, Thesleff, 2000). One reason for this could reside in the fact that they share common origins in terms of evolution, and as during embryogenesis substantial morphological structures are recapitulated, the position of the mesenchymal stem cells of the hair follicle is also found in the case of nails and teeth. Therefore, teeth may also be regenerated with cultivated cells of the peribulbar follicular or dental apparatus. By using the morphogenic features, a new or thicker nail or tooth may be induced in analogy to hair. Therefore, the present invention relates furthermore to the mesenchymal stem cells of the nail and the dental apparatus as a means for therapy and prophylaxis as well as the use of the stem cells for the preparation of a medicament for therapy and prophylaxis of diseases of the nail or dental apparatus as well as for gene therapy.

By means of the ability of the DSC cells to form new hair follicles or to add to dermal hair follicles which are already present, it is therefore possible to treat all types of hair loss and hair miniaturization. In addition to that, there is the long life span of the DSC cells according to the invention and their ability to be implanted without problems and thereby staying fully functional. The DSC cells of a hair follicle, the nail or the dental apparatus may be also used in gene therapy when the production of secretory substances is required. These cells may be genetically modified such that e.g. after transfection the cells would be competent to secrete the desired product. Via the skin, the product could be systematically distributed by means of the blood. As an example, the transfection of the DSC cells with an insulin gene may be mentioned. After implantation of these now insulin producing cells, the treatment of a diabetes mellitus would be possible. Many other examples for a deficiency of a secretion product (hormones, proteins, cytokines, chemokines, growth factors, lipo mediators) are known.

The following examples illustrate the invention and are not to be understood as limiting the scope of the invention.

Micro dissection: A whisker/vibrissa hair follicle from a mouse was at first separated into its portions by micro dissection. As shown in FIG. 3a, at first intact anagen hair were prepared under a dissection microscope. In the case of pigmented hair, a cross-sectional cut was performed through the hair at the upper pole of the pigment zone (FIG. 3b, arrows) and the cup shape-like attached hair bowl (DSC) was peeled away together with the dermal hair papilla (DP) (FIG. 3c). This tissue piece was everted (FIG. 3d) and the DP (FIG. 3e) was separated from the DSC (FIG. 3f). After the dissection the epithelial root sheaths (FIG. 3h) and the connective tissue coating (FIG. 3i) remained.

Cell culture: Subsequently, the dissected DSC was propagated in cell culture. AmnioMax C 100 basal medium (Gibco) and AmnioMax C100 supplement was used as medium. At first, the DSC were cultivated in 24-well-culture flasks (Falcon, Franklin Lakes, N.J., USA) in said medium under sterile conditions and standard conditions (37° C., 5% $CO_2$, 500 µl medium). After a few days, the cells grew out spontaneously and were detached with 200 µl/well trypsin-EDTA after they reached a confluent culture (termination of the trypsination with 260 µl Amniomax medium/well after detachment of all cells) and were transferred into 25 ml culture flasks (Greiner, Frickenhausen, Germany). For this, the cells were pooled, centrifuged at 1000 U/min for 10 minutes, the supernatant was discarded and the cells were resuspended in 5 ml Aminomax. The medium was exchanged every 3 days. AmnioMax C 100 basal medium (Gibco) and AmnioMax C100 supplement was used as medium. At first, the DSC were cultivated in 24-well-culture flasks (Falcon, Franklin Lakes, N.J., USA) in said medium under sterile conditions. After a few days, cells grew out spontaneously, proliferated and could be subcultivated in 25 ml culture flasks (Greiner, Frickenhausen, Germany) using standard methods.

Detection of the alkaline phosphatase: For in vivo analysis, tissues were deep-frozen, embedded in OCT reagent (Tissue tec, Sakura, Zoeterwounde, The Netherlands) and 6 µm thick frozen sections were prepared. The alkaline phosphatase was detected using alkaline phosphatase "fast red TR" substrate solution (Pierce Company, Rockford, Ill., USA: 10 mg fast red TR as supplied, 10 ml substrate buffer, 1.5 ml naphthole AS-MX phosphate concentrate as supplied) at pH 8.1 following the manufacturer's instructions. The development took place for 30 minutes in the absence of levamisole. For the detection of the alkaline phosphatase in vitro, the cells were cultivated on sterile cover slips, fixed in acetone and the reagent was used as described for the measurement of the alkaline phosphatase. The incubation period was 1 hour.

Induction of hair growth: After a few cell passages, the cells were still able to induce a new hair. After a small injury (scratch), $3–5\times10^6$ cells in 0.1 ml PBS were injected into the dermis of a mouse ear about 2 mm besides the wound using a sterile 16 gauge needle. For these experiments, the animals were anaesthetised with 1.66 ml xylazine hydrochloride (Rompun, Bayer Vital Leverkusen, Germany) in 10 ml ketamine-hydrochloride (Hexal, Holzkirchen, Germany). After this, it was observed for several weeks if there was new hair growth. After two months, hair growth was observed after implantation of DP and DSC, but not after implantation of DS cells. The hair growth continued for a period of 6 months, indicating that these clinical observations are not a transient phenomenon. Furthermore, it could be observed that already pre-existing hair became thicker after implantation (FIG. 6).

Confocal laser microscopy: Besides the biological characteristics of the induction of hair growth by DSC cells, the migration of the different cells was observed after implantation. For this, tissue was prepared from the three described morphological hair zones (DP, DS, DSC) of mice (STOCK TgN(GFPX)4Nagy). These mice were selected because all nucleus containing cells of these mice contain green fluorescent proteins. Cells from these tissues were cultivated and passaged over a period of 6 weeks. The three distinct cell types were injected into the ears of immune incompetent CbySmm.CB17-Prkdc$^{scid}$/J mice. In addition, cells from non fluorescent, GFP STOCK TgN(GFPX) 4Nagy, C3H/HeJ mice and PVG/OlaHsd rats were injected in the same manner. It was observed if there is new growth of hair or a thickening of already pre-existing hair. After 2-6 months, the animals were killed and the ears were embedded. For this, the tissues were fixed in 4% paraformaldehyde (Sigma, Deisenhofen, Germany) in $PBS^{-/-}$ for 2 hours, and subsequently rinsed with $PBS^{-/-}$ for several times. The tissue was embedded in "Tissue-Tek" at room temperature and stored for 24 hours at +4° C. in the dark. Subsequently, the tissues were cooled down slowly to −70° C. in a cellulose padded polystyrene box (so called "slow freezing technique"). At first, the tissue block was warmed to −20° C. for 30 minutes. Subsequently, sections between 20 and 40 µm were produced using a cryostat, which were put on microscope slides that were pretreated with 1% poly-L-lysine (Sigma, Deisenhofen, Germany). The drying was carried out at room temperature. Subsequently, the sections were once rinsed with $PBS^{-/-}$, before the sections were covered with $PBS^{-/-}$ or water containing cover medium, e.g. glycerol. After this, the tissues were analysed using a laser microscope of the company Zeiss (Gottingen, Germany), type LSM 410, at the wavelengths of 488 mn excitation, 500-520 nm emission, Z-axis in 2 µm intervals using an argon-krypton laser.

Subsequently, serial sections (20-40 µm) were carried out and analysed for the presence of GFP (=green fluorescent protein) expressing cells using the confocal laser microscope. By means of these experiments preliminary investigations could be confirmed that new hair growth is possible by the implantation of DP cells and that only the implanted cells form the new hair, whereas implanted DS cells did not result in the formation of hair but were visible in the dermis as diffuse, GFP expression cell population when using a confocal microscope. Implanted DP cells only led to the formation of a new dermal hair papilla but not to the formation of a follicular connective tissue coating. In contrast, the DSC cells formed both a new DP and a part of the follicular connective tissue (DS) coating. By the fact that the DSC cells may rebuild all dermal hair structures, whereas cells of the DP are not able to do so, it can be deduced that the DSC are less differentiated and more pluripotent than cells of the DP. For this reason, the DSC cells are the adult mesenchymal stem cells of the hair follicle. FIG. 4 illustrates the inductive characteristic of DSC cells. In summary, it could be observed as a result that the DSC cells are the putative stem cells from which the DP and the follicular connective tissue sheath are formed.

It could be shown that after implantation of DSC a new hair is formed and that implanted DSC cells form both a new DP and also a new connective tissue coating (DS). This was visible in the confocal microscope by the green fluorescence both in the zone of the DSC and the DP and the connective tissue sheath (DS). The analysis performed six months after injection of cells showed that GFP expressing cells were still present in the relevant hair follicle structures. The injected cells have a very slow cell cycle typical for stem cells and exhibit a regenerative capacity. There was no recruiting of non-GFP expressing dermal cells on the part of the host. Furthermore, single green fluorescent cells could be observed in pre-existing hair indicating that implanted DSC cells colonise existing DP thereby leading to a thicker hair.

References

Chuong C M, Hou L, Chen P J, Wu P, Patel N, Chen Y (2001) Dinosaur's feather and chicken tooth? Tissue engineering of the integument. Eur J Dermatol 11:286-292.

Hutchinson P E, Thompson J R (1997) The cross-sectional size and shape of human terminal scalp hair. Br J Dermatol 136:159-165

Hutchinson P E, Thompson J R (1999) The size and form of the medulla of human scalp hair is regulated by the hair cycle and cross-sectional size of the hair shaft. Br J Dermatol 140:438-445

Jahoda C A, Home K A, Oliver R F. Induction of hair growth by implantation of cultured dermal papilla cells. Nature. 1984 Oct 11-17; 311(5986):560-2.

Kligman A (1959) The human hair cycle. J Invest Dermatol 31:307-316

Messenger A G. The culture of dermal papilla cells from human hair follicles. Br J Dermatol. 1984 Jun; 110(6):685-9.

Oliver R F. The induction of hair follicle formation in the adult hooded rat by vibrissa dermal papillae. J Embryol Exp Morphol. 1970 Feb; 23(1):219-36. Paus R, Cotsarelis G (1999) The biology of hair follicles. N Engl J Med 341:491-497

Reynolds A J, Lawrence C, Cserhalmi-Friedman P B, Christiano A M, Jahoda C A. Trans-gender induction of hair follicles. Nature. 1999 Nov 4; 402(6757):33-4.

Sperling L C (1991) Hair anatomy for the clinician. J Am Acad Dermatol 25:1-17

Thesleff I (2000) Genetic basis of tooth development and dental defects. Acta Odontol Scand 58:191-194.

The invention claimed is

1. A method for obtaining a dermal sheath cup cell population, the method comprising the following steps:
   a) preparing adult vital hair,
   b) cleaving the hair prepared in step a),
   c) isolating the attached dermal sheath cup together with the dermal hair papilla,
   d) separating the dermal hair papilla from the dermal sheath cup,
   e) propagating isolated cells from the dermal sheath cup obtained in step d) in cell culture for more than one passage, and
   f) obtaining the dermal sheath cup cell population.

2. The method according to claim 1, wherein the hair follicle is derived from a mammal.

3. The method according to claim 2, wherein in the mammal is a mouse, a rat, a rabbit, a guinea pig, a goat, a pig, a bovine or a human.

4. An isolated adult dermal sheath cup cell population, obtainable by a method according to claim 1.

5. An isolated adult dermal sheath cup cell population having the characteristics of forming a completely new hair follicle, of migrating into a pre-existing hair papilla, of forming a part of the dermal connective tissue coating and of having a lower alkaline phosphatase activity than cells of the dermal papilla.

6. An isolated adult dermal sheath cup cell population, obtainable by a method according to claim 1, wherein said dermal sheath cup cell population has the characteristics of forming a completely new hair follicle, of migrating into a pre-existing hair papilla, of forming a part of the dermal connective tissue coating and of having a lower alkaline phosphatase activity than cells of the dermal papilla.

* * * * *

UNITED STATES PATENT AND TRADEMARK OFFICE
CERTIFICATE OF CORRECTION

PATENT NO.        : 8,431,400 B2
APPLICATION NO.   : 10/516031
DATED             : April 30, 2013
INVENTOR(S)       : Hoffmann et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 992 days.

Signed and Sealed this
Twenty-seventh Day of January, 2015

Michelle K. Lee
*Deputy Director of the United States Patent and Trademark Office*